(12) United States Patent
Onobori et al.

(10) Patent No.: US 12,085,240 B2
(45) Date of Patent: Sep. 10, 2024

(54) ILLUMINATION APPARATUS

(71) Applicant: HOYA CORPORATION, Tokyo (JP)

(72) Inventors: Kunihiko Onobori, Friedberg (DE); Tilman Schröter, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 30 days.

(21) Appl. No.: 18/013,153

(22) PCT Filed: Jun. 24, 2021

(86) PCT No.: PCT/IB2021/055587
§ 371 (c)(1),
(2) Date: Dec. 27, 2022

(87) PCT Pub. No.: WO2022/003503
PCT Pub. Date: Jan. 6, 2022

(65) Prior Publication Data
US 2023/0280001 A1    Sep. 7, 2023

(30) Foreign Application Priority Data
Jul. 3, 2020   (DE) ............ 10 2020 117 580.9

(51) Int. Cl.
*F21K 9/64*   (2016.01)
*A61B 1/06*   (2006.01)
(Continued)

(52) U.S. Cl.
CPC .............. *F21K 9/64* (2016.08); *A61B 1/0653* (2013.01); *F21W 2131/20* (2013.01);
(Continued)

(58) Field of Classification Search
CPC ..................... A61B 1/0653; A61B 1/0661
See application file for complete search history.

(56) References Cited

U.S. PATENT DOCUMENTS

| 11,559,194 B2 | 1/2023 | Onobori |
| 2006/0058584 A1 | 3/2006 | Hirata |

(Continued)

FOREIGN PATENT DOCUMENTS

| JP | 2004-363343 A | 12/2004 |
| JP | 2011-091158 A | 10/2008 |

(Continued)

OTHER PUBLICATIONS

Notice of Reasons for Refusal issued in Japanese Patent Application No. 2022-579880, dated Jan. 16, 2024, together with an English translation.

(Continued)

*Primary Examiner* — Eric T Eide
(74) *Attorney, Agent, or Firm* — GREENBLUM & BERNSTEIN, P.L.C.

(57) ABSTRACT

It is provided an illumination apparatus, comprising a first light source mounted on a board emitting first light having a first wavelength spectrum; a second light source mounted on the board emitting second light having a second wavelength spectrum; a phosphor layer converting at least a part of at least one of the first light and the second light into first converted light and second converted light, respectively; wherein the phosphor layer emits a remaining part of the first light, a remaining part of the second light, the first converted light, and the second converted light; the phosphor layer is in contact with the first and second light sources and continuous on the first and second light sources, and on a path on the board connecting the first and second light sources; the phosphor layer and the board surround the first light source and the second light source.

18 Claims, 10 Drawing Sheets

(51) Int. Cl.
*F21W 131/20* (2006.01)
*F21Y 113/10* (2016.01)
*F21Y 115/10* (2016.01)
*F21Y 115/30* (2016.01)

(52) U.S. Cl.
CPC ........ *F21Y 2113/10* (2016.08); *F21Y 2115/10* (2016.08); *F21Y 2115/30* (2016.08)

(56) References Cited

U.S. PATENT DOCUMENTS

| | | | |
|---|---|---|---|
| 2006/0152926 A1* | 7/2006 | Hama | A61B 1/07 362/231 |
| 2008/0089089 A1 | 4/2008 | Hama et al. | |
| 2009/0306478 A1* | 12/2009 | Mizuyoshi | A61B 1/07 600/178 |
| 2012/0200687 A1 | 8/2012 | Kikuchi | |
| 2013/0002167 A1 | 1/2013 | Van De Ven | |
| 2013/0076230 A1 | 3/2013 | Watanabe et al. | |
| 2019/0071506 A1 | 3/2019 | Barth et al. | |
| 2019/0388702 A1 | 12/2019 | Watanabe et al. | |
| 2021/0106211 A1 | 4/2021 | Onobori | |
| 2021/0267439 A1 | 9/2021 | Onobori et al. | |
| 2022/0225862 A1 | 7/2022 | Onobori | |
| 2023/0082243 A1 | 3/2023 | Onobori | |

FOREIGN PATENT DOCUMENTS

| | | |
|---|---|---|
| JP | 2008-258177 A | 5/2011 |
| JP | 2013-69980 A | 4/2013 |
| JP | 2018-41858 A | 3/2018 |

OTHER PUBLICATIONS

U.S. Appl. No. 18/013,140 to Kunihiko Onobori, which was filed Dec. 27, 2022.
U.S. Appl. No. 18/023,052 to Wolfgang Mayer et al., which was filed Feb. 24, 2023.
International Search Report issued in International Patent Application No. PCT/IB2021/055587, dated Sep. 22, 2021.
Notice of Reasons for Refusal issued in Japanese Patent Application No. 2022-579880, dated Jun. 25, 2024, together with an English translation.

* cited by examiner

ILLUMINATION APPARATUS

FIELD OF THE INVENTION

The present invention relates to an illumination apparatus for illuminating an object with different spectra. In particular, it relates to an illumination apparatus, which is useful in the tip portion of an endoscope, in particular an endoscope comprising a wide field of view objective lens.

BACKGROUND OF THE INVENTION

White Light (WL) and vascular pattern enhanced illumination (so called narrow band illumination which has illumination spectrum synchronized to hemoglobin absorption spectrum) are getting more common in endoscopic imaging. For energy effectiveness and to create a wider angle of light distribution, it is better to have the light source at the distal end of an endoscope without involving fiber optics. However, there is no off-the-shelf LED which has good spectrum for Vascular pattern enhanced illumination with micro size package (ex. 500 um×500 um).

In general, imaging with different colored light is known in the art. For example, there is white light imaging (WLI) and "spectrum imaging". In WLI, the object (such as a colon) is illuminated by white light. In contrast, in spectrum imaging, the object is illuminated with light having a spectral distribution different from that of white light. For example, spectrum imaging with a spectrum comprising substantially only violet and green light is known to be used for vascular pattern enhanced illumination.

FIG. 1 shows an illumination system for an endoscope according to the prior art which allows both WLI and spectrum imaging. This illumination system comprises a white LED (here shown as a blue LED with a yellow phosphor covering the blue LED) and, separated from the white LED, a violet LED and a green LED. In spectrum imaging, only the violet and green LEDs emit light. Thus, the emitted light has a gradient from violet on the left side via green violet to green on the right side. In WLI, only the white LED emits light.

Such illumination system has several disadvantages: the relative intensity of the violet and green lights varies with the position on the object. Furthermore, the illumination by the white light is at a different position on the object than the illumination by the violet and green LEDs. Thus, a doctor using the prior art endoscope cannot easily observe the same position under different illuminations. Still furthermore, quite some space is required to accommodate the 3 LEDs in the tip portion of the endoscope.

SUMMARY OF THE INVENTION

It is an object of the present invention to improve the prior art. Namely, according to an aspect of the present invention, there is provided an illumination apparatus according to the independent claim. Further aspects of the invention provide a rigid tip of an endoscope comprising the illumination apparatus, an endoscope comprising the illumination apparatus, and methods to manufacture the illumination apparatus. Further details are set out in the respective dependent claims.

According to some embodiments of the invention, at least one of the following advantages may be achieved:
the space required for the illumination apparatus enabling both WLI and spectrum illumination is reduced;
the configuration is easy to implement;
the color distribution is more homogeneous than according to the prior art;
a doctor may easily observe a position under different illuminations.

Further advantages become apparent from the following detailed description.

It is to be understood that any of the above modifications and the examples described below can be applied singly or in combination to the respective aspects to which they refer, unless they are explicitly stated as excluding alternatives.

BRIEF DESCRIPTION OF THE DRAWINGS

Further details, features, objects, and advantages are apparent from the following detailed description of preferred embodiments of the invention, which is to be taken in conjunction with the appended drawings, wherein.

DETAILED DESCRIPTION OF CERTAIN EMBODIMENTS

Herein below, certain embodiments of the present invention are described in detail as reference to the accompanying drawings, wherein the features of the embodiments can be freely combined with each other unless otherwise described. However, it is to be expressly understood that the description of certain embodiments is given by way of example only, and that it is by no means intended to be understood as limiting the invention to the disclosed details.

In the Figures, the same numerals designate corresponding components, which are distinguished by different letters. The Figures are schematic only. In particular, the sizes are not at scale. For example, the light sources (LEDs or emission ends of optical fibers) may be substantially a point.

According to some embodiment of the invention, at least two types of light sources having different peak wavelengths are arranged on a printed circuit board (PCB). For the reminder of the description, it is assumed that 2 types of LEDs are employed, but the number of types may be larger than 2. Light emitting ends of optical fibers with light emission devices (such as lasers or LEDs) configured to emit respective lights into the optical fibers may be employed as light sources instead of the LEDs. In this case, the light emission devices may be arranged at the proximal end of the endoscope. The light sources may be mixed: e.g., the light sources of the first type may be LEDs and the light sources of the second type may be emission ends of optical fibers. Hereinafter, LEDs are described as an example of light sources but the invention is not limited to LEDs as light sources.

In addition, a phosphor layer comprising one or more phosphors is arranged on the PCB and the LEDs. More in detail, the phosphor layer is in contact at least with the LEDs and a path on the PCB such that the phosphor layer and the PCB surround the LEDs. The phosphor layer is continuous over the LEDs and the path. Here, the term "surrounding" preferably means that the PCB and the phosphor layer enclose the LEDs from all sides, without any gap. However, the term "surrounding" also includes a case where one or more small gaps are provided within the PCB, and/or within the phosphor layer, and/or at the interface between the PCB and the phosphor layer. If such one or more gaps are present, they are arranged such that at least 95% of each of the lights emitted by the LEDs enters the phosphor layer or is absorbed by the PCB.

Figure 2:
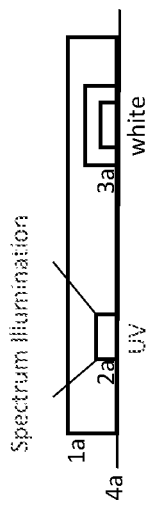
FIG. 2 shows a cross-section of a unit cell of an illumination apparatus according to some embodiments of the invention, used in spectrum illumination.

FIG. 2 shows a unit cell of an illumination apparatus according to some embodiments of the invention. The illumination apparatus comprises one or more unit cells. Each unit cell comprises a first LED 2a of a first type (such as a LED emitting UV light), and a second LED 3a, which emits a different spectrum, such as a white LED. The LEDs are mounted on one surface of a PCB 4a. The LEDs 2a and 3a of the unit cell illuminate the phosphor layer 1a comprising a phosphor. The phosphor converts at least a portion of the light from the first LED (first light) into first converted light. In addition, the phosphor may convert at least a portion of the light from the second LED (second light) into second converted light. The first converted light has a different spectrum than the first light. The second converted light, if any, has a different spectrum than the second light.

Figure 1:
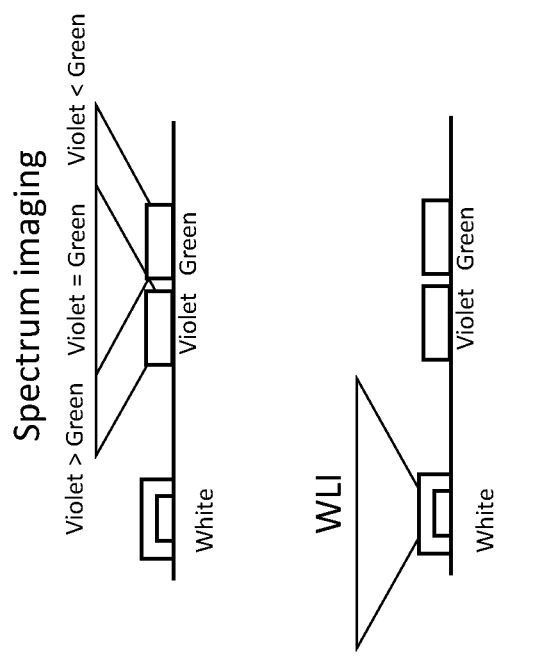
FIG. 1 shows an illumination system according to the prior art.
Figure 3:
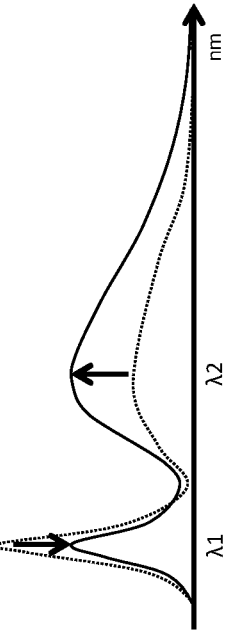
FIG. 3 shows an emission spectrum if the illumination apparatus of FIG. 2 is used in spectrum illumination.

For example, as shown in FIG. 3, in case of spectrum illumination, only the UV LED 2a illuminates the phosphor layer with light, while the white LED 3a is switched off. In this case, the emission spectrum comprises violet or deep blue light (sometimes also called UV light) from the LED 2a around wavelength (peak wavelength) $\lambda 3$ (e.g. 400 to 430 nm), and green light from the conversion by the phosphor in the exit layer 1a (for example of a wavelength around $\lambda 2$: 520 to 580 nm).

In white light illumination, only the second LED 3a illuminates light on the exit layer 1a, while the first LED 2a is dark. In this case, the white LED 3a is a phosphor covered blue LED which has an emission spectrum as shown by the dashed line in FIG. 5. That is, it has a high peak in the blue region ($\lambda 1$ about 440 to 460 nm) and a broad maximum in the green region around $\lambda 2$. Due to the conversion by the phosphor in the phosphor layer 1a, the intensity of the blue light around $\lambda 1$ is reduced and the broad maximum around $\lambda 2$ is enhanced and broadened. Thus, white light illumination is performed.

Figure 5:
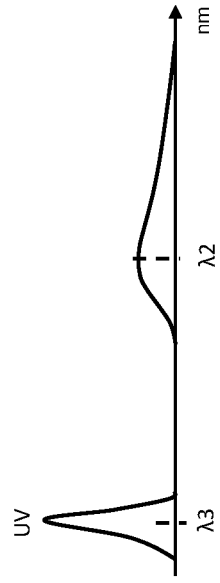
FIG. 5 shows the spectrum of emitted light if the illumination apparatus of FIG. 4 is used in WLI.

The spectra shown in FIGS. 3 and 5 are examples only. Other combinations of different types of LEDs combined with different types of phosphors fall under the scope of the present invention. Instead of a single type of phosphor, plural types of phosphor may be used in the phosphor layer. These different types of phosphors may be mixed or arranged in different layers.

Figure 4:
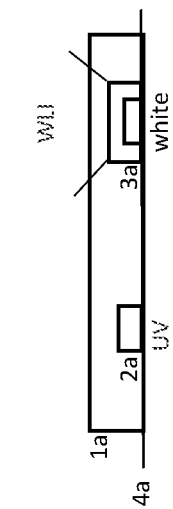
FIG. 4 shows the unit cell of the illumination apparatus according to FIG. 2 used in WLI.
Figure 7:
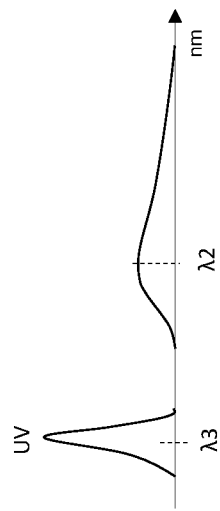
FIG. 7 shows the emission spectrum of the illumination apparatus of FIG. 6 used in spectrum illumination.

FIGS. 6 to 9 show another example of the units according to some embodiments of the invention, which correspond to FIGS. 2 to 5, except that the white LED 3a of FIGS. 2 and 4 is replaced by the blue LED 3b emitting light in the range of 440 to 460 nm. Since in this example the first LED 2b and the phosphor in the phosphor layer 1b are the same as in FIGS. 2 and 4, the spectrum in the case of spectrum illumination shown in FIG. 7 is the same as that shown in FIG. 3.

Figure 9:
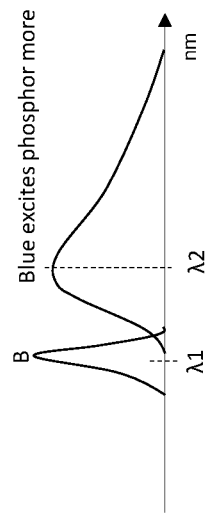
FIG. 9 shows the emission spectrum of the illumination apparatus of FIG. 8 used in WLI.
Figure 6:
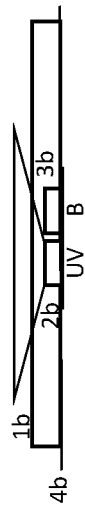
FIG. 6 shows a unit cell of another illumination apparatus according to some embodiments of the invention, used in spectrum illumination.
Figure 8:
FIG. 8 shows the illumination apparatus of FIG. 6 used in WLI.

However, in case of white light illumination, the blue LED 3b excites the phosphor more than the white LED 3a of FIGS. 2 and 4. Therefore, the emission spectrum in case of white light illumination has a larger and broader peak around $\lambda 2$, as shown in FIG. 9.

Figure 11:
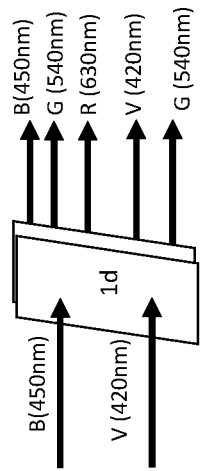
FIG. 11 shows another example of a phosphor layer which may be used according to some embodiments of the invention.
Figure 10:
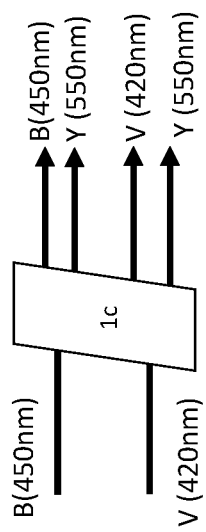
FIG. 10 shows another example of a phosphor layer which may be used according to some embodiments of the invention.

FIGS. 10 and 11 shows further examples of phosphor layers 1c and 1d which may be used according to some embodiments of the invention. As shown in FIG. 10, the LEDs emit blue light (peak wavelength about 450 nm) and violet light (peak wavelength about 420 nm). The phosphor in the phosphor layer converts parts of both of these lights into yellow light (peak wavelength about 550 nm). As shown in FIG. 11, the phosphor layer 1d comprises plural types of phosphor. In addition to the phosphor of the phosphor layer 1c of FIG. 10, a second type of phosphor converts part of the blue light from the respective LED into red light (peak wavelength about 630 nm). Thus, the output light from the phosphor layer 1d, if only the blue LED is switched on, is substantially white (comprises RGB in sufficient amounts). The conversion efficiency of the second phosphor for the violet light into red light is very small. Hence, the output light, if only the violet LED is switched on, is basically the same as for the phosphor layer 1d of FIG. 10.

Figure 12:
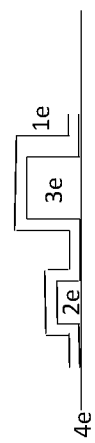
FIG. 12 shows an illumination apparatus according to some embodiments of the invention.

In FIGS. 2, 4, 6, and 8, the phosphor layer 1 has a flat emission surface. The emission surface is opposed to the surface facing the PCB. However, this is not mandatory. For example, the phosphor layer 1e may have a constant thickness, as shown in FIG. 12. Due to the thickness of the LEDs, in this case, the emission surface is not flat. In some embodiments, neither the emission surface of the phosphor layer 1 is flat nor does the phosphor layer 1 have a constant thickness. For example, in such embodiments, the unevenness of the surface of the PCB 4 on which the LEDs 2 and 3 are mounted, may be partially levelled out.

In some embodiments, plural unit cells each comprising at least a respective first LED 2 of a first type and a respective second LED 3 of a second type different from the first type (having a different peak wavelength) are arranged on the PCB 4 and covered by the common phosphor layer 1. In each of the unit cells, the first and second LEDs are disposed in the same way. The unit cells may be arranged in e.g. in a (straight or curved) line.

In some embodiments, the unit cells are arranged in a circle or a segment of a circle. In some of these embodiments, the illumination apparatus comprising the plural unit cells of two types of LEDs arranged on a PCB and a common phosphor layer comprising one or more phosphors is arranged around an objective lens configured to image an object space. The illumination apparatus is arranged to illuminate at least a part of this object space.

Figure 13:
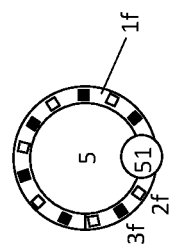
FIG. 13 shows a plan view on a rigid tip of an endoscope comprising an illumination apparatus according to some embodiments of the invention.

Such an arrangement is shown in FIG. 13. FIG. 13 shows the rigid tip of an endoscope in plan view (seen from the object space; the phosphor layer and an optional transparent lid covering the illumination apparatus are removed). The LEDs 2f, 3f, surround the objective lens 5 in the center. In the bottom part of the plan view, a working channel 51 is shown.

The PCB may comprise an adhesive in order to attach the phosphor layer to the PCB. The adhesive may or may not comprise the phosphor. If the adhesive does not comprise the phosphor, it should be rather thin. For example, a maximum thickness of the adhesive is not larger than 10% of a maximum thickness of a light source (LED) among the first light source and the second light source having a smallest maximum thickness among the first light source and the second light source. Preferably, the ratio is not larger than 5%. Preferably, the adhesive, if any, is arranged such that at least 95% of the light emitted by the LEDs enter the phosphor layer. More preferably, at least 98% or even 100% of the emitted light enters the phosphor layer.

According to some embodiments, if the phosphor layer is locally parallel to the surface of the PCB facing the phosphor layer, the amount of phosphor in the direction perpendicular to the surface of the PCB is substantially constant. I.e., it varies by not more than 20%, preferably not more than 10%, and still more preferably by not more than 5% around an average value. If the illumination apparatus comprises plural unit cells, in some embodiments, the amount of phosphor in the direction vertical to the surface of the PCB facing the phosphor layer may vary correspondingly to the arrangement of the unit cells. E.g., if the unit cells are arranged periodically, the amount of phosphor in the vertical direction may vary with the same period. The surface of the PCB facing the phosphor layer is the surface on which the LEDs are mounted.

In the thickness direction of the phosphor layer, the concentration of the phosphor may be substantially constant. However, according to some embodiments, the concentration of the phosphor may have peaks. If the phosphor layer comprises plural phosphors, they may be distributed homogeneously in the phosphor layer, or they may be arranged in different levels in the thickness direction.

Preferably, the surface of the PCB facing the phosphor layer may be substantially flat. Variations of the planarity e.g. due to a wiring and/or an adhesive may not exceed 10% of a maximum thickness of a light source (LED) among the first light source and the second light source having a smallest maximum thickness among the first light source and the second light source. Preferably, the ratio is not larger than 5%. However, the invention is not limited to a substantially flat surface of the PCB. Some embodiments of the invention may comprise a curved surface of the PCB facing the phosphor layer.

If the light sources are LEDs, the PCB may comprise a circuit for controlling the LEDs. For this purpose, the LEDs are electrically connected to terminals arranged on the PCB. In some embodiments, each LED may be controlled separately. In some embodiments, at least the LEDs of the first type may be controlled separately from the LEDs of the second type. "Controlling" means at least switching on and off. It may additionally mean setting the light intensity and/or the color emitted by the respective LED. The same applies to other light sources generating the light locally (on the PCB), e.g. if the light sources are laser diodes.

The LEDs may be mounted on the PCB in any known way, such as a surface mounted device (SMD) or in flip-chip bonding.

As explained hereinabove, the illumination apparatus is preferably arranged in a rigid tip of an endoscope for inserting into a lumen of a human body. Such a rigid tip may comprise an objective lens, and the illumination apparatus may be arranged around the objective lens. Furthermore, the rigid tip may comprise an image sensor, a working channel, etc. The rigid tip may be directly or indirectly (via an angulation segment) connected to a flexible or rigid shaft for inserting into the lumen of the human body such that embodiments of the invention also encompass an endoscope. In some embodiments, the rigid tip may be used stand-alone (i.e., without being connected to a shaft of an endoscope). Thus, the illumination apparatus may be employed in so called "capsule endoscopy".

However, the invention is not limited to illumination apparatuses in rigid tip portions of an endoscope for inserting into a lumen of a human body. It may be applied to other endoscopes (not suitable for being inserted into a lumen of a human body, such as endoscopes for pipelines), too. It may be applied even outside from endoscopes, e.g. to illuminate an object space of a camera such as CCTV.

According to some embodiments of the invention, there are several options to manufacture such an illumination apparatus. They are explained with LEDs as examples of light sources but they are not limited to LEDs.

Figure 14:
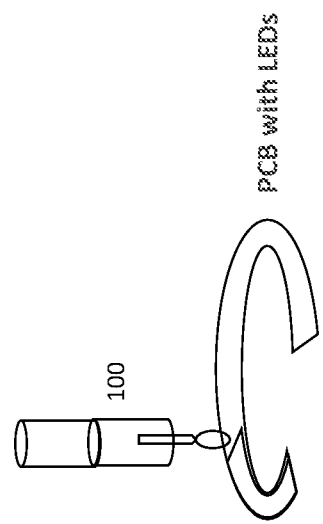
FIG. 14 illustrates a manufacturing method according to some embodiments of the invention.

A first manufacturing method is shown in FIG. 14. The phosphor is solved in a fluid or gel and the fluid or gel is dispensed, by a dispenser 100, on the PCB on which the light sources are mounted. In detail, the fluid or gel is dispensed at least on the LEDs and on a path connecting the LEDs such that the PCB and the fluid or gel surround the LEDs. Then, the fluid is dried or the gel is cured such that the phosphor layer comprising the phosphor is obtained.

The fluid or gel must have a sufficient viscosity such that it remains, before the drying or curing is finished, substantially in the area where the fluid or gel was dispensed. If the light sources generate the light locally (e.g. the light sources are LEDs, laser diodes, etc.), prior to the dispensing, the light sources are electrically connected to terminals arranged on the PCB. If an adhesive is needed to adhere the phosphor (or the medium comprising the phosphor) to the PCB, the adhesive may be applied as a thin layer to the PCB and the LEDs prior to the dispensing.

An example of the solvent to form the fluid or gel comprising the phosphor is silicone. An example of the adhesive is a polymer.

The fluid or gel may be dispensed once or plural times on each position in order to form the phosphor layer. If the fluid or gel is dispensed plural times, the phosphor(s) in the fluid or gel may be the same, or different phosphors may be included in the fluid or gel for different dispense operations. Thus, the phosphor layer may have an internal layered structure of different phosphors.

Figure 15:
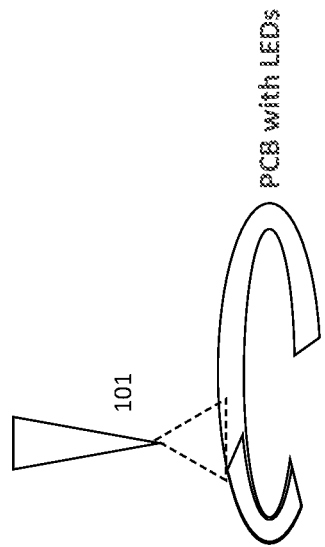
FIG. 15 illustrates a manufacturing method according to some embodiments of the invention.

A second manufacturing method is shown in FIG. 15. According to FIG. 15, the fluid, in which the phosphor is solved, is sprayed on the PCB by a sprayer 101 and then dried. Otherwise, the second manufacturing method corresponds to the first manufacturing method.

Figure 16:
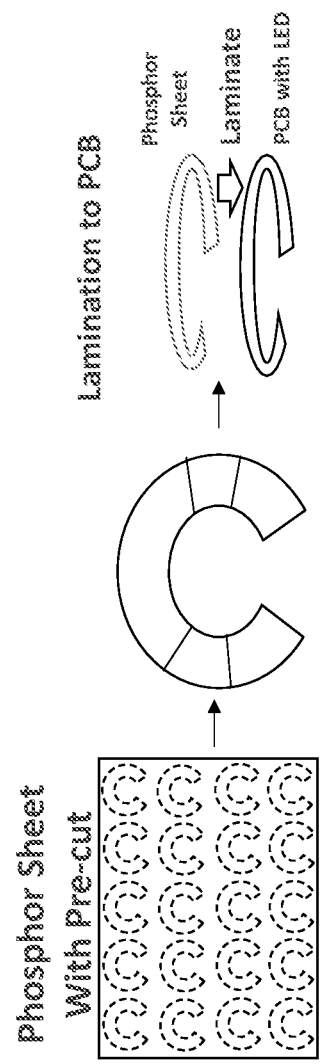
FIG. 16 illustrates a manufacturing method according to some embodiments of the invention.

FIG. 16 shows a third manufacturing method. In the third manufacturing method, a phosphor sheet is prepared, wherein the phosphor sheet comprises the phosphor dispersed in a medium (e.g. silicone) or the phosphor sheet consists of the phosphor. The phosphor sheet may be much larger than a PCB on which the light sources are mounted. Then, pieces are cut out of the phosphor sheet having a shape corresponding to that of the phosphor layer. Here, the term "corresponding to" means that the pieces may have the same shape as the phosphor layer, or that they may have a shape which takes level differences to the LEDs, shrinkage due to thermal expansion etc. into account. I.e., the cut out pieces may have a slightly different shape than the finalized phosphor layer.

Then, one of the cut-out pieces is applied to one PCB on which the light sources are mounted (and electrically connected to terminals of the PCB, if needed). The cut-out pieces should preferably have some flexibility in order to adapt to the surface of the PCB on which the LEDs (light sources) are mounted. If an adhesive is needed to adhere the cut-out piece with the PCB and/or LEDs, it may be applied as a thin layer to the PCB and/or LEDs, and/or it may be applied as a thin layer to the phosphor sheet (either before the pieces are cut out or on the cut-out pieces). An example of an adhesive usable in this manufacturing method is an adhesive transfer tape such as 467 MP of 3M.

Figure 17:
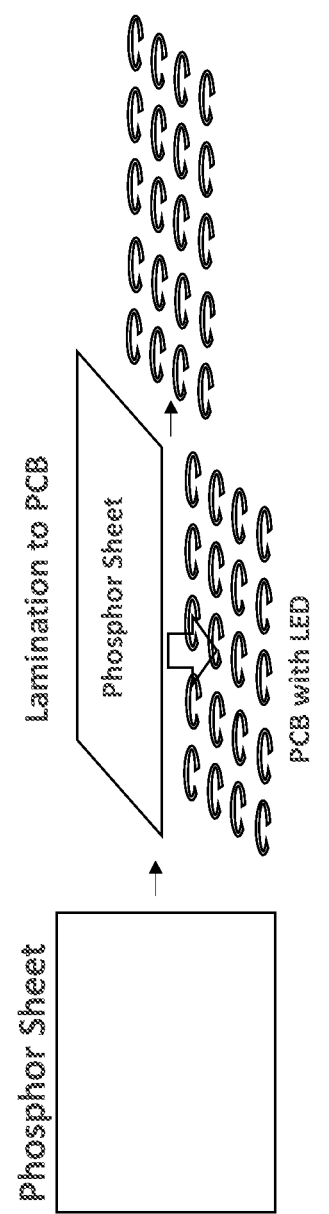
FIG. 17 illustrates a manufacturing method according to some embodiments of the invention.

FIG. 17 illustrates a fourth manufacturing method, which is a variant of the third manufacturing method. According to FIG. 17, the phosphor sheet is laminated on a plurality of PCBs on which the light sources are mounted (and electrically connected to terminals of the PCB, if needed). An adhesive may be applied on the phosphor sheet and/or the PCBs/LEDs. Then, the unnecessary portions of the laminate are removed by cutting out. Thus, the phosphor layer covers the entire PCB on which the light sources are mounted. Otherwise, the fourth method corresponds to the third method.

In some embodiments (not illustrated), the PCBs of plural illumination apparatuses may be respective parts of a large PCB. In these embodiments, the PCBs of the illumination apparatuses may be cut out from the large PCB in the step of cutting out the phosphor layers according to the fourth method. Thus, since the PCB and the phosphor layer of each illumination apparatus are cut out in the same step, one manufacturing step may be saved.

Figure 18:
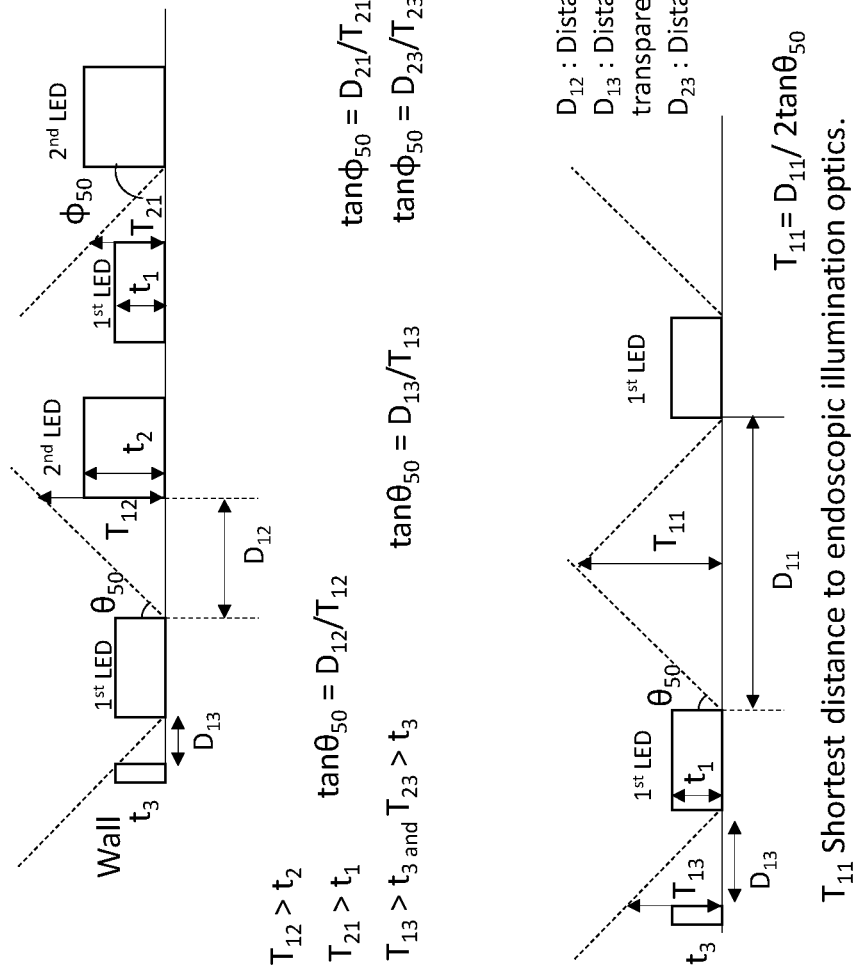
FIG. 18 illustrates a determination of a preferred minimum thickness of the phosphor layer.
Figure 19:
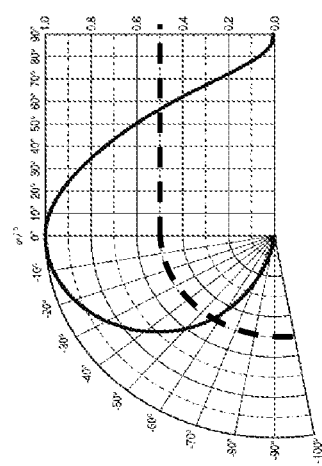
FIG. 19 shows an example of a radiation distribution of a LED.

FIG. 18 illustrates a derivation of a minimum thickness the phosphor layer should preferably have to ensure that the illumination apparatus provides a substantially homogenous illumination. In the bottom part of FIG. 18, it is shown that each position of the emission surface of the phosphor layer should be illuminated by at least one of the first LEDs with at least 50% of its intensity. This condition is fulfilled if the minimum thickness $T_{11}=D_{11}/2*\tan\theta_{50}$. $D_{11}$ denotes a distance between two adjacent first LEDs, and $\theta_{50}$ denotes a radiation angle at which the emission of the first LED is 50% of its maximum emission. The value of $\theta_{50}$ may by obtained from the radiation characteristics of the first LED. A typical example is shown in FIG. 19. In this example, $\theta_{50}$ is about 55°.

The same consideration applies correspondingly to the second LEDs. If the respective minimum thicknesses are different, the phosphor layer should preferably have a minimum thickness which is the larger one of the minimum thicknesses for each of the two types of LEDs. The radiation angle at which the emission of the second LED is 50% of its maximum emission is denoted $\Phi_{50}$.

In the top part of FIG. 18, additional considerations are illustrated in order to determine a maximum value of $\theta_{50}$ and $\Phi_{50}$ (at given distances between the LEDs and given heights of the LEDs and non-transparent walls, if any), or to determine minimum distances between the LEDs (at given values of $\theta_{50}$ and $\Phi_{50}$ and given heights of the LEDs and non-transparent walls, if any), or to determine maximum heights of the LEDs and non-transparent walls, if any (at given values of $\theta_{50}$ and $\Phi_{50}$ and given distances between the LEDs). Namely, the height of the emission ray with 50% intensity should be higher than the height of the neighbored LED or wall (if any). In the top part of FIG. 18:

$T_{12}$ denotes the height of this ray from the first LED at the position of the edge of the second LED facing the first LED;

$T_{21}$ denotes the height of this ray from the second LED at the position of the edge of the first LED facing the second LED;

$T_{13}$ denotes the height of this ray from the first LED at the position of the edge of a neighbored wall facing the first LED;

$T_{23}$ denotes the height of this ray from the second LED at the position of the edge of a neighbored wall (not illustrated) facing the first LED;

$D_{12}$ denotes the shortest distance between the first LED and the second LED;

$D_{21}$ denotes the shortest distance between the second LED and the first LED ($D_{12}=D_{21}$);

$D_{13}$ denotes the shortest distance between the first LED and the neighbored wall; and $D_{23}$ denotes the shortest distance between the second LED and the neighbored wall (not illustrated).

If the first LED, second LED, and the wall have thicknesses $t_1$, $t_2$, and $t_3$, the relationships $T_{12}>t_2$; $T_{21}>t_1$; $T_{13}>t_3$; and $T_{23}>t_3$ are obtained. In the limit case, the conditions for $\theta_{50}$ and $\Phi_{50}$ are $\tan\theta_{50}=D_{12}/T_{12}$; $\tan\theta_{50}=D_{13}/T_{13}$; $\tan\Phi_{50}=D_{21}/T_{21}$; and $\tan\Phi_{50}=D_{23}/T_{23}$.

The conditions derived in the top part and the bottom part of FIG. 18 are preferred according to some embodiments of the invention but not mandatory. For example, in some embodiments only a subset of these conditions or even none of these conditions may be fulfilled.

Some embodiments of the invention with the light emission devices arranged at the distal end of an endoscope are advantageous over other illumination systems where the light emission devices are arranged in a box at the proximal end, and the light is guided to the distal end via one or more optical fibers because of the higher efficiency regarding power conversion. Even if the light sources are located in a control body at the proximal end of the endoscope the space is limited.

Furthermore, arranging a common phosphor system for violet and blue LEDs is preferable (but not mandatory) at the distal end of the endoscope because of the following considerations with respect to an arrangement at the proximal end:

White-LED (WLED) has a standard phosphor covered package. However, the phosphor causes scattering which means it is difficult to focus the light efficiently into the fiber optics. For violet LED, a standard phosphor package does not exist. It has to be customized with considerable costs, and this phosphor will scatter the light, like WLED.

In contrast, if the phosphor layer is placed on the distal-end, the scattering of the light by the phosphor is even advantageous to distribute the light into a wider angle to illuminate a wide field of view. The light emission devices (such as LEDs) may be arranged in the distal end, too (behind the phosphor layer), or they may be arranged at the proximal end, and the light is guided from the light emission devices through one or more optical fibers to the distal end. In this case, the emission ends of the optical fibers act as the light sources, as described above.

The invention claimed is:

1. An illumination apparatus, comprising
a board comprising an adhesive;
a first light source mounted on the board, wherein the first light source is configured to emit first light having a first wavelength spectrum;
a second light source mounted on the board, wherein the second light source is configured to emit second light having a second wavelength spectrum different from the first wavelength spectrum; and
a phosphor layer comprising a phosphor arranged to convert at least a part of at least one of the first light and the second light into first converted light and second converted light, respectively, wherein a third wavelength spectrum of the first converted light is different from the first wavelength spectrum, and a fourth wavelength spectrum of the second converted light is different from the second wavelength spectrum; wherein
the phosphor layer is configured to emit a remaining part of the first light, a remaining part of the second light, and the at least one of the first converted light and the second converted light;
the phosphor layer is in contact with the first light source and the second light source and continuous on the first light source, on the second light source, and on a path on the board connecting the first light source and the second light source;
the phosphor layer and the board surround the first light source and the second light source;
the adhesive adheres to the phosphor layer; and
a maximum thickness of the adhesive is not larger than 10% of a maximum thickness of a light source among the first light source and the second light source having a smallest maximum thickness among the first light source and the second light source.

2. The illumination apparatus according to claim 1, comprising
a plurality of the first light sources mounted on the board, each configured to emit the first light;
a plurality of the second light sources mounted on the board, each configured to emit the second light; wherein
the phosphor layer is in contact with each of the first light sources and each of the second light sources and continuous on each of the first light sources, on each of the second light sources, and on a path connecting the first light sources and the second light sources;
the phosphor layer and the board surround the first light sources and the second light sources.

3. The illumination apparatus according to claim 1, wherein at least one of
the phosphor layer covers the entire board;
100% of the first light enter the phosphor layer; and
100% of the second light enter the phosphor layer.

4. The illumination apparatus according to claim 1, wherein
the first wavelength spectrum comprises mainly blue light;
the second wavelength spectrum comprises mainly violet light and/or ultraviolet light;
the phosphor is configured to convert a first portion of the blue light into yellow light such that the first output light appears to be white;
the phosphor is configured to convert a second portion of the violet light and/or ultraviolet light into the yellow light;
the first portion is larger than the second portion.

5. The illumination apparatus according to claim 1, wherein
the first wavelength spectrum comprises mainly blue light;
the second wavelength spectrum comprises mainly violet light and/or ultraviolet light;
the phosphor is configured to convert a first portion of the blue light into green and red light such that the first output light appears to be white;
the phosphor is configured to convert a second portion of the violet light and/or ultraviolet light into the green light.

6. The illumination apparatus according to claim 1, wherein,
in the phosphor layer, the phosphor is dispersed in a medium.

7. The illumination apparatus according to claim 1, wherein at least one of:
the first light source is a light emitting diode or a laser diode; and
the second light source is a light emitting diode or a laser diode.

8. The illumination apparatus according to claim 7, wherein at least one of:
if the first light source is a light emitting diode or a laser diode, the board comprises first terminals and the first light source is electrically connected to the first terminals;
if the second light source is a light emitting diode or a laser diode, the board comprises second terminals and the second light source is electrically connected to the second terminals.

9. The illumination apparatus according to claim 8, wherein
the first light source is controllable via the first terminals;
the second light source is controllable via the second terminals; and
the first light source is controllable separately from the second light source.

10. The illumination apparatus according to claim 1, wherein at least one of
the first light source is an emitting end of a first optical fiber and the illumination apparatus comprises a first light emitting device configured to input the first light into the first optical fiber;
the second light source is an emitting end of a second optical fiber and the illumination apparatus comprises a second light emitting device configured to input the second light into the second optical fiber.

11. The illumination apparatus according to claim 1, wherein the phosphor layer comprises plural phosphors.

12. A method of manufacturing the illumination apparatus according to claim 1, comprising
providing the board on which the first light source and the second light source are mounted;
dispensing a fluid or a gel comprising the phosphor on the first light source, on the second light source, and on the path on the board connecting the first light source and the second light source;

curing the gel or drying the fluid to obtain the phosphor layer.

13. The method according to claim 12, further comprising flowing the phosphor gel prior to the curing.

14. A method of manufacturing the illumination apparatus according to claim 1, comprising
    providing the board on which the first light source and the second light source are mounted;
    spraying a fluid comprising the phosphor on the first light source, on the second light source, and on the path on the board connecting the first light source and the second light source;
    drying the sprayed fluid to obtain the phosphor layer.

15. A method of manufacturing the illumination apparatus according to claim 1, comprising
    providing the board on which the first light source and the second light source are mounted;
    preparing a sheet comprising the phosphor such that, in a plan view, the sheet has a shape corresponding to a shape of the first light source, the second light source, and the path on the board connecting the first light source and the second light source;
    attaching the sheet to the board, the first light source and the second light source such that the sheet covers the first light source, the second light source, and the path to obtain the phosphor layer.

16. A method of manufacturing the illumination apparatus according to claim 1, comprising
    providing the board on which the first light source and the second light source are mounted;
    attaching a sheet comprising the phosphor to the board such that the sheet covers the first light source, the second light source, and the path on the board connecting the first light source and the second light source;
    cutting off a part of the sheet extending beyond the board to obtain the phosphor layer.

17. A rigid tip portion of an endoscope or a capsule endoscope for inserting into a lumen of a human body, comprising an objective lens and the illumination apparatus according to claim 1 arranged to illuminate, by at least one of the first output light and the second output light, at least a portion of an object space imaged by the objective lens.

18. An endoscope comprising the rigid tip portion according to claim 17 and a flexible or rigid shaft for inserting into the lumen of the human body, wherein the rigid tip portion is directly or indirectly connected to the flexible or rigid shaft.

* * * * *